US 7,238,359 B2

(12) United States Patent
Hasnain et al.

(10) Patent No.: US 7,238,359 B2
(45) Date of Patent: Jul. 3, 2007

(54) ANTIGEN ORF RV2430C AND A METHOD THEREOF

(75) Inventors: Seyed Ehtesham Hasnain, Andhra Pradesh (IN); Rakesh Kumar Choudhary, Andhra Pradesh (IN)

(73) Assignees: Centre for DNA Fingerprinting and Diagnostics; An Autonomous Centre for the Department of Biotechnology, Ministry of Science & Technology, Government of India, Hyderabad (IN)

( * ) Notice: Subject to any disclaimer, the term of this patent is extended or adjusted under 35 U.S.C. 154(b) by 0 days.

(21) Appl. No.: 11/199,719

(22) Filed: Aug. 9, 2005

(65) Prior Publication Data

US 2006/0078566 A1     Apr. 13, 2006

Related U.S. Application Data

(60) Provisional application No. 60/600,322, filed on Aug. 9, 2004.

(51) Int. Cl.
*A61K 39/04* (2006.01)
*A61K 39/02* (2006.01)
*A61K 38/00* (2006.01)
*C12Q 1/00* (2006.01)

(52) U.S. Cl. .................. 424/248.1; 424/9.1; 424/9.2; 424/184.1; 424/185.1; 424/190.1; 424/234.1; 435/4; 530/300; 530/350

(58) Field of Classification Search ............. 424/9.1, 424/9.2, 184.1, 185.1, 190.1, 234.1, 248.1; 435/4; 530/300, 350
See application file for complete search history.

*Primary Examiner*—Rodney P Swartz
(74) *Attorney, Agent, or Firm*—John P. White; Cooper & Dunham LLP

(57) ABSTRACT

The present invention relates to a PPE family antigenic protein Rv2430c of SEQ ID No. 1; a set of three high antigenic index peptides of SEQ ID Nos. 2 to 4; an antigenic ORF Rv2430c of SEQ ID No. 5 and lastly a method of inducing immune response against *Mycobacterium tuberculosis* in a subject in need thereof, said method comprising step of: introducing PPE antigenic protein Rv2430c of SEQ ID No. 1 into the subject and inducing immune response against *Mycobacterium tuberculosis*.

9 Claims, 8 Drawing Sheets

```
Conf: [confidence bars]
Pred: ----[helix]----[helix]----
Pred: CCCCCCCHHHHHHHHCCCCCCHHHHHHHHHHHHHHHHHHHH
 AA: MHPEAYPPEVNSAMIYAGPGPDSMLAAARAWRSLDVBMTA
         10        20        30        40

Conf: [confidence bars]
Pred: [helix]----[helix]----
Pred: HHHHHHHHHHHHHCCCCCHHHHHHHHHHHHHHHHHHHH
 AA: VQRSFNRTLLSLMDAHAGPVVMQLMEAAKPFVRWLTDLCV
         50        60        70        80

Conf: [confidence bars]
Pred: [helix]----[helix]----
Pred: HHHHHHHHHHHHHHHHHHCCCCCHHHHHHHHHHHHHHHHH
 AA: QLSEVERQIHEIVRAYEWAHHDMVPLAQIYNNRAERQILI
         90       100       110       120

Conf: [confidence bars]
Pred: [helix]
Pred: HHHHHHHHHHHHHHHHHHHHHHHHHHHHHHHHHHHHHHHH
 AA: DHNALGQPTAQIADLDQEYDDFWDBDGEVMRDYRLRVSDA
        130       140       150       160

Conf: [confidence bars]
Pred: [helix]----
Pred: HHHCCCCCCCCCCCCCCCCCCCCCCCCCCCCCCCCCCC
 AA: LSKLTPWKAPPPIAHSFVLVAPVSPSTASSRTDT
        170       180       190
```

Legend:
- helix
- strand
- coil

Conf: confidence of prediction
Pred: predicted secondary structure
AA: target sequence

Fig. 1 B

US 7,238,359 B2

ANTIGEN ORF RV2430C AND A METHOD THEREOF

This application claims the benefit of U.S. Provisional Application No. 60/600,322, filed Aug. 9, 2004, the contents of which are hereby incorporated by reference.

FIELD OF THE INVENTION

The present invention relates to a PPE family antigenic protein Rv2430c of SEQ ID No. 1; a set of three high antigenic index peptides of SEQ ID Nos. 2 to 4; an antigenic ORE Rv2430c of SEQ ID No. 5 and lastly a method of inducing an immune response against *Mycobacterium tuberculosis* in a subject in need thereof, said method comprising the step of: introducing PPE antigenic protein Rv2430c of SEQ ID No. 1 into the subject and inducing an immune response against *Mycobacterium tuberculosis*.

BACKGROUND OF THE INVENTION

Figure 7:
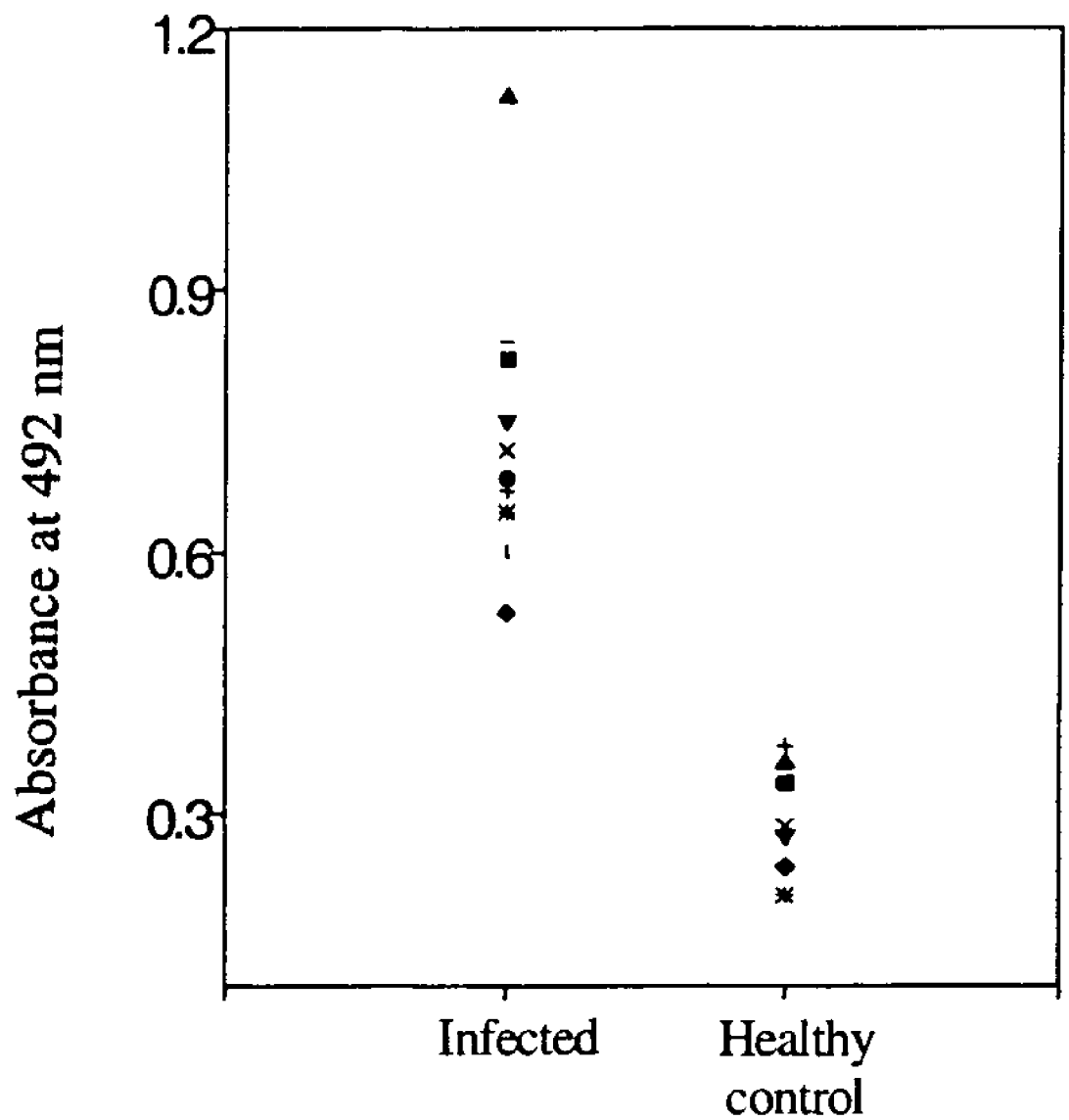

The genome of *Mycobacterium tuberculosis* codes for two large families of glycine rich proteins namely PE and PPE [1]. The names PE and PPE derive from the motifs Pro-Glu (PE) and Pro-Pro-Glu (PPE) found near the N-terminus of these proteins. Both the families have a conserved N-terminal domain followed by a C-terminal domain which varies in sequence and length. The PE family of proteins is divided in several subfamilies, the largest of these being the repetitive PGRS class, which contains 61 members. The PGRS proteins have a high Glycine content which arises as a result of multiple repetitions of Gly-Gly-Ala or Gly-Gly-Asn motifs. The 69 members of the PPE family have a conserved N-terminal domain followed by C-terminal segments that vary markedly in sequence and length. The PPE proteins fall in three groups, one of which has the MPTR subgroup marked by the presence of tandem copies of Asn-X-Gly-X-Gly-Asn-X-Gly (SEQ ID No. 6). The second group has a conserved motif at position 350 whereas third subgroup proteins have a common PPE domain. A few studies have suggested the functional importance of the PE/PPE [1, 2] family of proteins and it is widely believed that these proteins could be a source of antigenic variation in *Mycobacterium tuberculosis [*3-7]. Subcellular fractionation and immunoelectron microscopy studies have revealed that some of the members of the PE/PPE family are located on the cell wall fraction of *Mycobacterium tuberculosis [*8, 9].

OBJECTS OF THE PRESENT INVENTION

The main object of the present invention is to identify novel antigenic regions in the genome of M.tb.

Another main object of the present invention is to develop a method to identify antigenic regions in the genome of M.tb.

Yet another object of the present invention is to develop a method of treating tuberculosis.

Yet another object of the present invention is to develop a method of inducing an immune response against *Mycobacterium tuberculosis.*

Yet another object of the present invention is to identify high antigenic index peptides in ORF Rv2430c.

SUMMARY OF THE PRESENT INVENTION

The present invention relates to a PPE family antigenic protein Rv2430c of SEQ ID No. 1; a set of three high antigenic index peptides of SEQ ID Nos. 2 to 4; an antigenic ORF Rv2430c of SEQ ID No. 5 and lastly a method of inducing an immune response against *Mycobacterium tuberculosis* in a subject in need thereof, said method comprising the step of: introducing PPE antigenic protein Rv2430c of SEQ ID No. 1 into the subject and inducing an immune response against *Mycobacterium tuberculosis.*

BRIEF DESCRIPTION OF THE ACCOMPANYING DRAWINGS

FIG. 1 (A). In silico analysis of Rv2430c using Protean 4.0. The presence of stretches of alpha helix is shown. X axis denotes the length in amino acids. (B). Secondary structure prediction of Rv2430c using PSIPRED (SEQ ID No. 10). Output from the PSIPRED web server displays a high content of alpha helix for Rv2430c.

FIG. 2. SDS-PAGE analysis of recombinant Rv2430c expressed in *E.coli.* The PPE protein was expressed in M15pREp4 strain of *E.coli* and was eluted with 500 mM imidazole after on-column refolding. The different lanes are: 1, Uninduced culture; 2, Induced culture; 3, Protein molecular size marker; 4, Purified protein. Arrowheads indicate the molecular sizes of the markers whereas the arrow indicates the purified protein.

FIG. 3. Rv2430c has alpha helical structure as revealed from far-UV CD spectra analyses. Far-UV CD spectrum was recorded in 25 mM Tris-Cl, pH 8.0 with 0.9% NaCl in the range of 190 to 250 nm. Cell of path length 0.02 cm was used for recording the Far-UV spectra. Ellipticity was represented in millidegrees. The spectrum obtained is characteristic of a alpha helical protein. FIG. in Inset shows the percentage composition of different secondary structures in Rv2430c. Data obtained from the CD spectra were calculated to get the percentage composition of secondary structure. Rv2430c shows a content of 81% of alpha helical structure.

FIG. 4. The aromatic residues in Rv2430c are present in a hydrophobic region. Purified PPE protein was incubated in the presence and absence of 8M urea for 2 hr at room temperature and the fluorescence emission spectra were recorded by exciting the protein at 280 nm and recording the emission spectra in the range of 300 nm-400 nm. The lines indicating folded protein and unfolded protein are duly represented. A significant red shift in absorption was observed.

FIG. 5. In silico analysis of the PPE ORFs. Only the ORFs belonging to sub group 3 and less than or equal to 200 amino acids in length were subjected to analysis. The presence of stretches of high antigenic index are shown. The X axis denotes the ORF length in amino acids while the Y axis represents the antigenic index.

FIG. 6A. The hypothetical PPE ORF Rv2430c is transcribed. RNA extracted from the virulent H37Rv laboratory strain of *Mycobacterium tuberculosis* was used in an RT-PCR reaction. A 597 bp RT-PCR product was observed after electrophoresis in a 1% agarose gel (lane 1). Lane M depicts the 100 bp DNA molecular size marker run alongside. Arrowhead indicates the position of the 597 bp PCR product.

FIG. 6B. Expression and purification of the recombinant PPE protein. The recombinant protein was expressed in M15pREP4 strain of *E.coli* and was purified to homogeneity using the NiNTA protein purification kit. Lane 1 is the marker, Lane 2 is the purified protein. Arrowhead indicates the position of the 23 kDa protein.

FIG. 7. The recombinant Rv2430c PPE protein elicits strong antibody response in *M.tuberculosis* infected patients as opposed to healthy controls. ELISA reactivity of IgG anti-Rv2430c antibodies were assayed in sera of either *M.tuberculosis* infected patients or healthy controls (p<0.0001).

Figure 8:
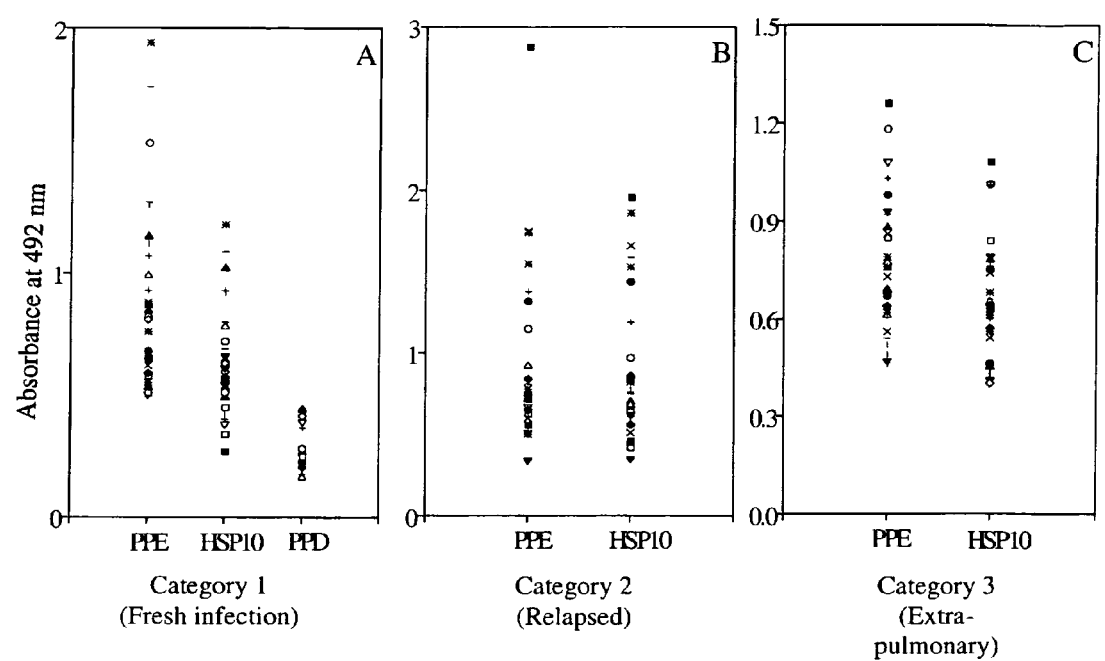

FIG. 8. PPE Rv2430c protein shows strong reactivity to sera from all three patient categories. Reactivity to both recombinant Rv2430c and Hsp10 of *M.tuberculosis* in the three categories of patients was estimated by ELISA. The patients belonging to Categories 2 (FIG. 8B) and 3 (FIG. 8C) displayed similar antibody responses to both the antigen. However, the antibody responses of Category 1 patients (FIG. 8A) were higher to the Rv 2430c as compared to the Hsp10 (p<0.003) or PPD (p<0.0001).

Figure 9:
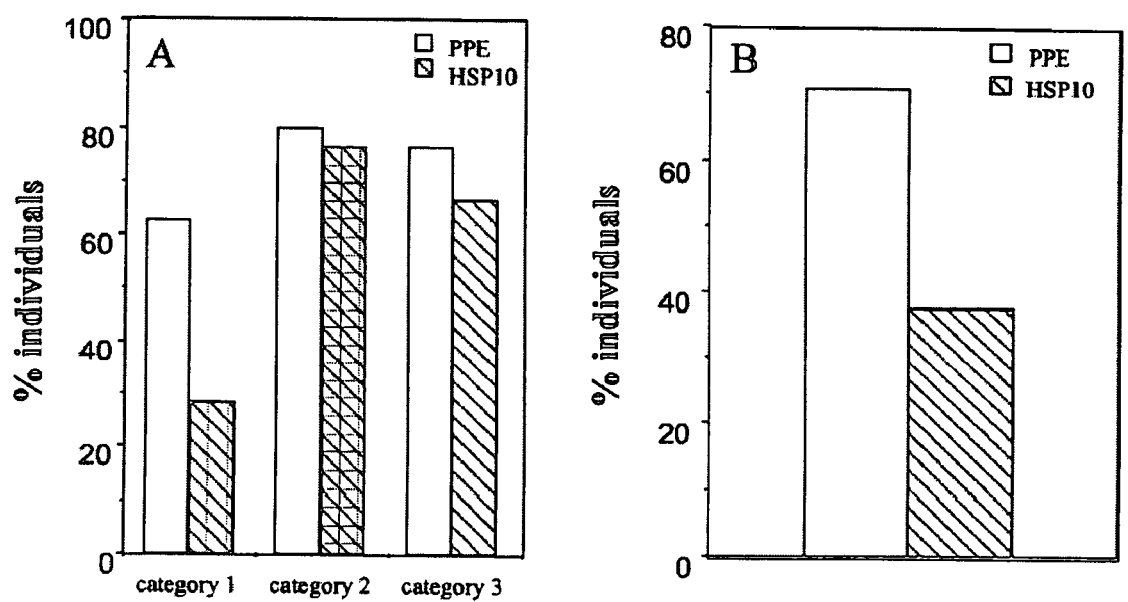

FIG. 9. Serological sensitivity of PPE Rv2430c and Hsp10 as a function of % of individuals. A. Results described in FIG. 8 were recalculated as percentage individuals showing absorbance value above 0.65 at 492 nm. The anti-IgG response against Rv2430c or Hsp10 was compared for all the three categories of patients studied. A higher percentage of individuals belonging to Category 1 show stronger reactivity to Rv2430c than the Hsp10 but for the other two categories the values were comparable. B. Percentage individuals showing anti-IgM antibody above 0.5 absorbance at 492 nm in Category 1. A higher percentage of individuals show anti-IgM antibody more than 0.5 absorbance against Rv2430c as compared to the Hsp10.

DETAILED DESCRIPTION OF THE INVENTION

Accordingly, the present invention relates to a PPE family antigenic protein Rv2430c of SEQ ID No. 1.

In still another embodiment of the present invention, the protein shows strong B-cell immune response.

In yet another embodiment of the present invention, the protein has high content of alpha helices.

In still another embodiment of the present invention, the protein is more antigenic than Hsp10 and PPD.

One more embodiment of the present invention provides a set of three high antigenic index peptides, the amino acid sequence of which is set forth in SEQ ID Nos. 2 to 4.

Still another embodiment of the present invention provides an antigenic ORF Rv2430c, the amino acid sequence of which is set forth in SEQ ID No. 5.

In yet another embodiment of the present invention, a method of inducing an immune response against *Mycobacterium tuberculosis* in a subject in need thereof comprises the steps of:
  a. introducing PPE antigenic protein Rv2430c of SEQ ID No. 1 into the subject and
  b. inducing an immune response against *Mycobacterium tuberculosis*.

In still another embodiment of the present invention, the subject is an animal or human being.

The antigenic ORF Rv2430c of SEQ ID NO: 5 is as given below:

```
>M. tuberculosis H37Rv|Rv2430c|PPE41: 585 bp -
PPE FAMILY PROTEIN
atgcatttcgaagcgtacccaccggaggtcaactccgccaacatatatgccggccccggt cctgactcgatgttggctgccgccagggcgtggaggtcgttggatgtggaaatgacggcc gtgcagaggtcgttcaaccgaacgctgctgtctctgatggacgcctgggcgggtccagtg gtgatgcagttgatggaggcagccaagccgtttgtcaggtggctgaccgacctctgtgtg cagctgtctgaggtcgagaggcagatccacgagatcgtgcgggcctatgaatgggcacat cacgatatggtgccccctggcgcagatctacaacaaccgtgctgagaggcagattctgatc gacaacaacgcgcttgggcaattcactgcgcagatcgccgacctcgaccaagaatatgac gacttctgggacgaggacggagaggtgatgagggactacaggcttcgggtgtcggatgcg ttgtcgaagttgactccgtggaaggcgccgccgccgatcgcccacagtaccgtgttggtc gcaccggtgtcacccagcacggcgtcatcgcgtacagacacttag
```

A PPE family antigenic protein Rv2430c of SEQ ID NO.: 1 is as given below:

```
>M. tuberculosis H37Rv|Rv2430c|PPE41: 194 aa -
PPE FAMILY PROTEIN
MHFEAYPPEVNSANIYAGPGPDSMLAAARAWRSLDVEMTAVQRSFNRTLLSLMDAWAGPV

VMQLMEAAKPFVRWLTDLCVQLSEVERQIHEIVRAYEWAHHDMVPLAQIYNNRAERQILI

DNNALGQFTAQIADLDQEYDDFWDEDGEVMRDYRLRVSDALSKLTPWKAPPPIAHSTVLV

APVSPSTASSRTDT
```

Figure 5:
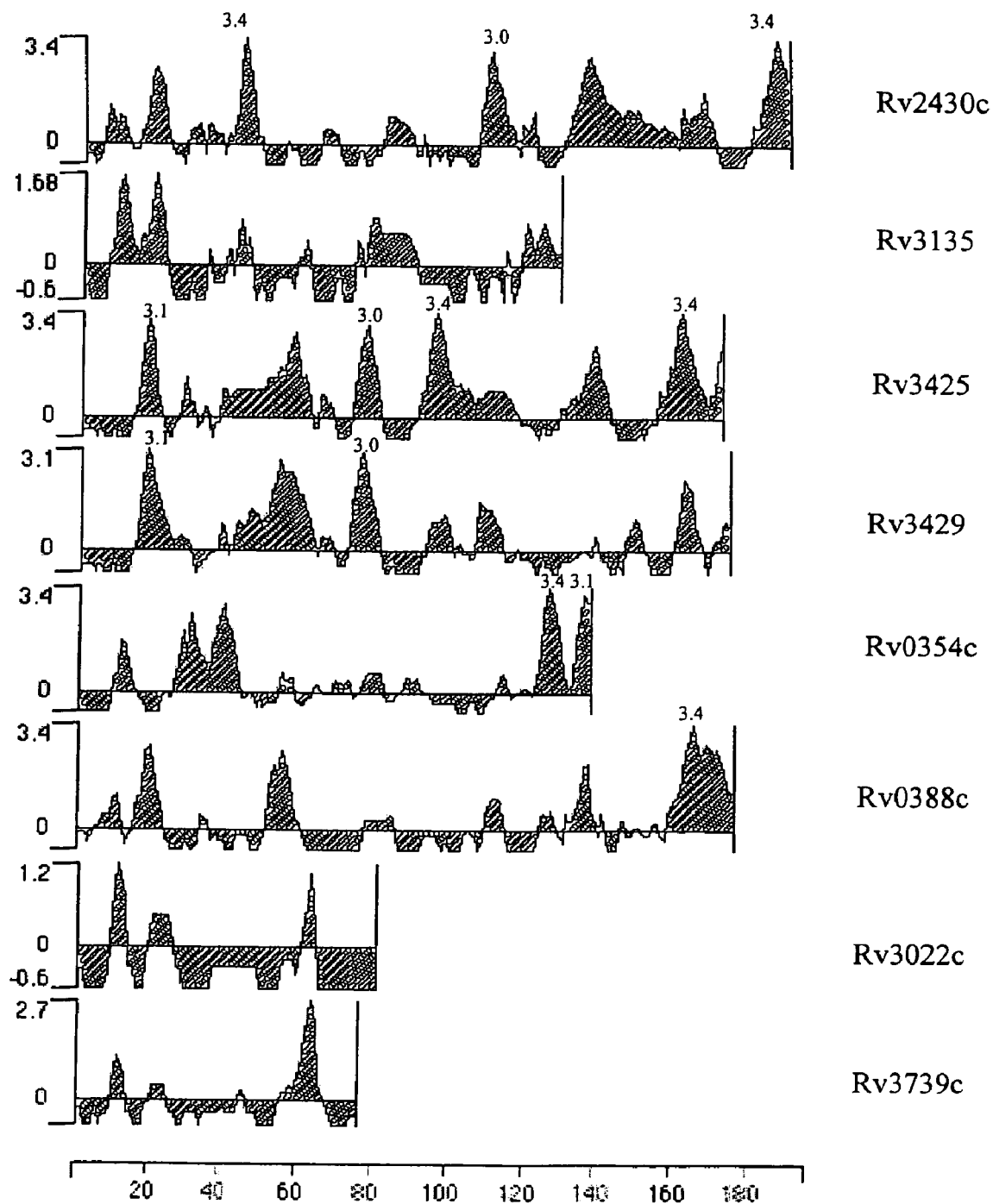

A set of three [3] high antigenic index peptides of SEQ ID NOS: 2 to 4 are as given below. The peaks 1, 2 and 3 reflect the high antigenic peptides of ORF Rv2430c as reflected in FIG. 5.

```
Peak 1 - SEQ ID NO.: 2
Ala 40, Val 41, Gln 42, Arg 43, Ser 44, Phe 45,
Asn 46, Arg 47, Thr 48, Leu 49, Leu 50.
```

-continued

Peak 2 - SEQ ID NO.: 3
Tyr 110, Asn 111, Asn 112, Arg 113, Ala 114,
Glu 115, Arg 116, Gln 117, Ile 118, Leu 119,
Ile 120.

Peak 3 - SEQ ID NO.: 4
Pro 185, Ser 186, Thr 187, Ala 188, Ser 189,
Ser 190, Arg 191, Thr 192, Asp 193, Thr 194.

Though there have been several reports about the structural characteristics of antigens from *M.tuberculosis* [10-15], there is no information regarding the biochemical or biophysical features of the PE/PPE family of proteins. We recently demonstrated the immunodominant nature of recombinant Rv2430c, a member of the PPE family, based on its reactivity with the sera of patients obtained from three well classified categories of TB patients, namely 1) fresh infection cases 2) cases with relapsed tuberculosis and 3) extrapulmonary cases, and a negligible reactivity with the sera obtained from healthy controls. In this study we report the purification, refolding and biophysical characterization of the recombinant Rv2430c protein expressed in *E.coli*.

About 10% of the genome of *Mycobacterium tuberculosis* (M.tb) codes for the PE and PPE family of proteins (30), which are glycine rich and are exclusive to M.tb. The 69 members of the PPE protein family have a conserved N-terminal domain that comprises ~180 amino acids followed by C-terminal segments that vary markedly in sequence and length. These proteins fall in three groups, one of which constitutes the MPTR class characterized by the presence of multiple, tandem copies of the motif Asn-X-Gly-X-Gly-Asn-X-Gly (SEQ ID No. 6). The second subgroup contains a characteristic well conserved motif Gly-X-X-Ser-Val-Pro-X-X-Trp (SEQ ID No. 7) around position 350 and the third group proteins are unrelated except for the presence of the common PPE domain. The sub-cellular location of a few PPE proteins is known (29, 48) and in only one case (30), that is of a lipase (Rv3097), has a function been suggested. There are few studies supporting the notion that PE/PPE proteins could be of functional importance (30, 46). It is widely speculated that they could be responsible for generating antigenic variation (24, 27, 29, 31, 35, 50). However, it has not been well documented what consequences the PPE family proteins, unique in their protein sequence and possible structure, may have on the immune system. Furthermore, a qualitative and quantitative immune response of PPE proteins in a clinical setting has not been shown. Since 180 amino acid residues in the N-terminal region of PPE proteins are conserved, it is interesting to speculate that the variation in the sequence and length in the C terminal region could represent a source of antigenic variability.

Based on in silico analysis and DNA microarray expression data (47), we selected an ORF, Rv2430c displaying a high antigenic index and evaluated its importance in eliciting an immune response in a panel of human sera obtained from three well classified categories of patients namely: a) reporting for the first time with TB, b) presenting a relapse of TB, and c) extrapulmonary cases. Clinically healthy human sera was used as a control to compare the immunological response to this protein. ELISA using the recombinant protein showed good specificity and sensitivity suggesting that this PPE family ORE Rv2430c induces a strong B cell response in infected subjects.

Accordingly, the present invention relates to purification, biophysical characterization, and treatment of tuberculosis that involves recombinant PPE protein coded by hypothetical ORE Rv2430c. Its particular PPE ORE induces a strong B cell response as compared to that generated by M.tb Hsp10 or PPD pointing to the immunodominant nature of this protein.

In silico and web based analyses of Rv2430c: In silico analysis of the Rv2430c was carried out using the Protein analysis software (Protean 4.0, Lasergene Navigator, DNASTAR Inc., Madison, Wis.). Predict protein (cubic.bioc.columbia.edu/predictprotein) and PSIPRED (bioinf.cs.ucl.ac.uk/psiform.html) were used for web based analyses.

Expression and purification of the recombinant protein coded by Rv2430c: The Rv2430c was cloned and expressed as previously described [16]. Recombinant plasmid PQE30Rv2430c carrying Rv2430c as a N-terminal histidine tagged fusion was transformed into the host M15pREP4 strain of *E. coli* and induced for expression by 1 mM IPTG. Cells were harvested 3 hours post induction. The harvested cells were suspended in Buffer A (25 mM Tris-Cl, pH 8.0 containing 8M urea and 0.9% NaCl) and incubated on an end-to-end shaker for 30 minutes at room temperature for lysis. The lysate was centrifuged at 13000 rpm for 30 minutes and the supernatant was then incubated with pre-equilibriated Ni-NTA slurry (Qiagen Inc., USA) for 15-20 minutes with gentle agitation to maximize the binding of the recombinant protein. The protein bound to slurry was then packed into a column. The bound protein was then subjected to on-column refolding by using a 250 ml gradient of buffer A and Buffer B (25 mM Tris, pH 8.0, 5 mM imidazole, 1 mM glutathione and 0.1M L-Arginine hydrochloride) at a flow rate of 1 ml/min using Acta-Prime chromatographic unit (Pharmacia Biotech). At the end of the gradient, the column was further washed with 50 ml of buffer B and then eluted with 25 mM Tris, pH 8.0 containing 500 mM imidazole. The homogeneity of the eluted protein was confirmed by 12% SDS-PAGE and the purified protein was dialyzed extensively at 4° C. against 25 mM Tris HCl pH 8.0 containing 0.9% NaCl. Protein was quantified by Pierce Micro BCA Protein Assay Reagent kit (Pierce, USA) and was subsequently used for spectroscopic analyses.

Circular Dichroism (CD) Spectroscopy. CD measurements were carried out on a spectropolarimeter (JASCO-715, JAPAN) using a 0.02-cm cell at 0.2-nm intervals and a two-nanometer bandwidth. Spectra were signal averaged by adding at least 4 accumulations. The base line was corrected by subtracting the spectra of respective buffer blank obtained under identical conditions. Percentage of secondary structure was calculated using the web based programme K2D (embl-heidelberg.de/~andrade/k2d). The concentration of protein used was 1 mg/ml.

Fluorescence spectroscopy: 20 μg of purified recombinant Rv2430c protein was incubated in the presence or absence of 8M urea for 2 hr at room temperature and the fluorescence emission spectra (300-400 nm) were recorded by exciting the protein at 280 nm using Perkin-Elmer LS-3B spectrofluorimeter at a slit width of 10 nm and scan speed of 50 nm/sec.

In silico analysis of Rv2430c. In silico pattern search analysis of the PPE family was carried out to classify the various ORFs into three subgroups. ORFs equal to or less than 200 amino acids and belonging to the third subgroup of the PPE family were further analysed using the protein analysis software (Protean 4.0, Lasergene Navigator, DNASTAR Inc., Madison, Wis.) to calculate their antigenic index.

RNA extraction and Reverse Transcriptase PCR. RNA was extracted from $1\times10^9$ $H_{37}Rv$ cells, cultured in vitro in Middlebrook 7H9 media supplemented with ADC, as per the Qiaquick total RNA extraction kit (Qiagen Inc., USA) and dissolved in 50 µl of nuclease free water and stored at −70° C. till further use. First strand synthesis was carried out using AMV reverse transcriptase. This was followed by heat denaturation to inactivate the enzyme. Subsequent second strand synthesis was performed using Tfl polymerase. The PCR product was visualized by electrophoresis in 1% agarose gel.

Expression and purification of the recombinant protein coded by Rv2430c. Genomic DNA of H37Rv was extracted using the Genome Extraction kit provided by Epicentre Technologies, USA as described earlier (49). The Rv2430c gene was PCR amplified from the genomic DNA of $H_{37}Rv$ using upstream (5'-GGATCCATGCATFTTCGAAGCG-TAC-3') (SEQ ID No. 8) and downstream primer (5'-AAGCTTCTAAGTGTCTGTACGCGATGA-3') (SEQ ID No. 9). BamHI and HindIII sites were incorporated in the 5' and 3' ends of the primers, respectively. The purified fragment was ligated into the pGEMT-easy vector (Promega Inc., USA) and recombinant clone carrying the Rv2430c insert was confirmed by DNA sequencing (ABI Prism 377 DNA Sequencer, PE Biosystems, USA). The insert was then subcloned as a BamHI and HindIII fragment into the PQE30 expression vector (Qiagen Inc., USA), to generate the plasmid construct PQERv2430c carrying Rv2430c as a N-terminal histidine tagged fusion. PQERv2430c was transformed into the host M15pREP4 strain of E. coli. A single colony of E.coli M15pREP4 strain harbouring PQERv2430c was inoculated in 5 ml of LB broth with the appropriate antibiotics (Ampicillin 100 µg/ml and Kanamycin 25 µg/ml) and grown overnight at 37° C. with constant agitation. 100 µl of this overnight culture was inoculated into 5 ml of LB broth with the appropriate antibiotics and grown until $0D_{590}=0.6$ at which time the expression was induced with 1 mM IPTG. A separate aliquot of uninduced culture was kept as a control. Cells were harvested 3 hours post induction, suspended in 1×SDS sample buffer and denatured by heating at 100° C. for 10 mm. The recombinant protein was purified to homogeneity as per the QIAExpressionist kit (Qiagen Inc., USA).

Serological characterization of the recombinant protein. ELISAs were performed in 96 well microtitre plates (Corning, Costar) coated with the recombinant Rv2430c protein. After overnight incubation at 4° C. the plates were washed thrice with PBS buffer and blocked with 200 µl of blocking buffer (PBS containing 1% BSA) for 1 hour at 37° C. The plates were then washed thrice with the PBS-Tween wash buffer (0.05% Tween 20 in 1×PBS, pH 8.0). and incubated for 1 hour at 37° C. with human sera (1:200 dilution in blocking buffer). The plates were washed with PBS-Tween and further incubated with either anti-human IgG-horseradish peroxidase (HRP) or anti-human IgM-HRP (Sigma, USA). HRP activity was detected using a chromogenic substance o-phenylenediamine tetrahydrochloride (Sigma, USA) in citrate-phosphate buffer (pH 5.4) and 1 µl/ml $H_2O_2$ (Qualigens, India). The reactions were terminated using IN $H_2SO_4$ and the absorbance values were measured at 492 nm in ELISA reader (BioRad, USA).

Study population. Serum samples were obtained from 92 TB patients reporting to the Mahavir Hospital and Research Centre, Hyderabad, India, and 10 clinically healthy donors. These 92 patients belonged to three well defined categories. Category 1 (n=32) comprised of patients who had contracted the pathogen for the first time and had no history of TB treatment. Category 2 (n=30) comprised of patients with relapsed tuberculosis, i.e who were treated earlier for TB but the symptoms resurfaced after the completion of the treatment. Category 3 (n=30) were patients with extrapulmonary tuberculosis in which the disease was confirmed by tissue biopsy. In the case of Category 1 and Category 2 patients, diagnosis was confirmed by the examination of the sputum (acid-fast bacillus smear positive). Clinically healthy donors were M.bovis BCG vaccinated. The study was carried out after approval from the Institute Bioethics Committee.

Statistical analysis. Student's t-test was used for analysis of statistical significance (p-value). Graphpad Quickcalcs (Online t-test calculator, graphpad.com/quickcalcs/ttest1.cfm) was used for this purpose.

Figure 1A:
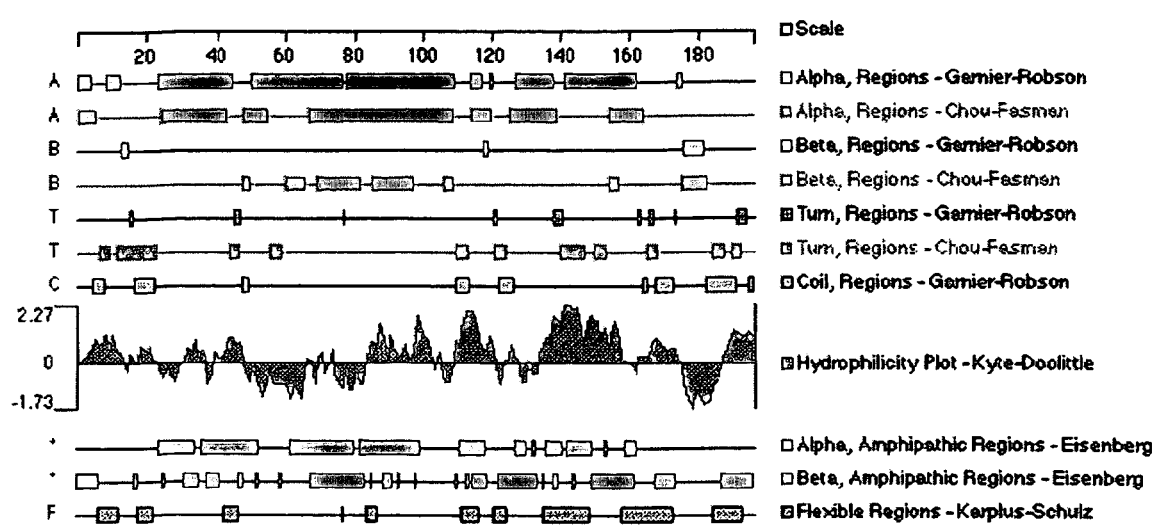

In silico analysis predicts a high content of alpha helices within PPE ORF Rv2430c: In silico and web based analysis of the PPE family comprising of all three groups was carried out (Table 1). It appears that while most of them have an irregular structure, the remaining ones have α helical structure. Given the fact that microarray data indeed pointed to the likely importance of a few members of this family under stress conditions, their function is largely unknown. We focussed on Rv2430c as it was demonstrated to induce a strong B cell response. Detailed computational analyses of Rv2430c predicted regions of high antigenic index with corresponding hydrophilicity and surface probability. Secondary structure prediction employing Protean 4.0 reveals a very high content of α helical structure in Rv2430c. This is evident from both the Gamier-Robson and Chou-Fasman methods of secondary structure prediction (FIG. 1A). Web based analysis of Rv2430c using PSIPRED similarly revealed a predominant α helical composition with a high prediction score (FIG. 1B). Similar results were obtained with Predict protein (76% α helix, data not shown).

Table 1: Results of in silico and web based analysis of the PPE ORFs belonging to all the three groups. [a]Microarray data were obtained from Tuberculist (genolist.pasteur.fr/TubercuList). [b]In silico analysis was carried out using the Protein analysis software, PROTEAN, DNASTAR. (R indicates irregular or random structure).

TABLE 1

Results of in silico and web based analysis of the PPE ORFs belonging to all the three groups.

| ORF | Amino acids | Microarray data[a] | In silico prediction[b] | Suggested function |
|---|---|---|---|---|
| MPTR (Subgroup1) | | | | |
| Rv0304c | 2204 | | R | Unknown |
| Rv0305c | 963 | | Alpha | Unknown |
| Rv0355c | 3300 | | R | Unknown |
| Rv0442c | 487 | | Alpha | Unknown |
| Rv0755c | 645 | | Alpha | Unknown |
| Rv0878c | 443 | | Alpha | Unknown |
| Rv1135c | 618 | | Alpha | Unknown |
| Rv1548c | 678 | | R | Unknown |
| Rv1753c | 1053 | | R | Unknown |
| Rv1917c | 1459 | | R | Unknown |
| Rv1918c | 987 | | R | Unknown |
| Rv2353c | 354 | | R | Unknown |
| Rv2356c | 615 | | Alpha | Unknown |
| Rv2608 | 580 | | Alpha | Unknown |
| Rv3159c | 590 | mRNA identified in starvation model [22] | Alpha | Unknown |
| Rv3343c | 2523 | | R | Unknown |
| Rv3347c | 3157 | | R | Unknown |
| Rv3350c | 3716 | | R | Unknown |
| Rv3533c | 582 | | R | Unknown |
| Rv3558 | 552 | | R | Unknown |

TABLE 1-continued

Results of in silico and web based analysis of the PPE ORFs belonging to all the three groups.

| ORF | Amino acids | Microarray data[a] | In silico prediction[b] | Suggested function |
|---|---|---|---|---|
| Motif around position 350 (Subgroup 2) | | | | |
| Rv0915c | 423 | | R | Unknown |
| Rv1039c | 391 | mRNA identified in starvation model [22] | R | Unknown |
| Rv1168c | 346 | | R | Unknown |
| Rv1196 | 391 | mRNA identified in starvation model [22] | R | Unknown |
| Rv1361c | 396 | | Alpha | Unknown |
| Rv1706c | 394 | | R | Unknown |
| Rv1787 | 365 | | R | Unknown |
| Rv1789 | 393 | | R | Unknown |
| Rv1790 | 353 | | R | Unknown |
| Rv1801 | 423 | mRNA identified in starvation model [22] | R | Unknown |
| Rv1802 | 463 | | Alpha | Unknown |
| Rv1807 | 399 | | R | Unknown |
| Rv1808 | 409 | mRNA identified in starvation model [22] | R | Unknown |
| Rv1809 | 468 | mRNA identified in starvation model [22] | R | Unknown |
| Rv2352c | 391 | | R | Unknown |
| Rv2768c | 394 | | R | Unknown |
| Rv2770c | 382 | | R | Unknown |
| Rv2892c | 408 | | Alpha | Unknown |
| Rv3125c | 391 | | R | Unknown |
| Rv3136 | 380 | mRNA identified in starvation model [22] | R | Unknown |
| Rv3532 | 406 | | R | Unknown |
| Others (Subgroup3) | | | | |
| Rv0096 | 463 | | R | Unknown |
| Rv0256c | 556 | mRNA identified in starvation model [22] | R | Unknown |
| Rv0280 | 536 | | Alpha | Unknown |
| Rv0286 | 513 | | Alpha | Unknown |
| Rv0354c | 141 | mRNA identified in starvation model [22] | R | Unknown |
| Rv0388c | 180 | | Alpha | Unknown |
| Rv0453 | 518 | | R | Unknown |
| Rv1387 | 539 | mRNA identified in starvation model [22] and in response to acidic conditions [23] | Alpha | Unknown |
| Rv1705c | 385 | | R | Unknown |
| Rv1800 | 655 | | Alpha | Unknown |
| Rv2108 | 243 | | Alpha | Unknown |
| Rv2123 | 473 | | R | Unknown |
| Rv2430c | 194 | | Alpha | Antigenic protein |
| Rv3018c | 434 | | R | Unknown |
| Rv3021c | 358 | | R | Unknown |
| Rv3022c | 82 | | R | Unknown |
| Rv3135 | 132 | | R | Unknown |
| Rv3144c | 409 | | R | Unknown |
| Rv3425 | 176 | | Alpha | Unknown |
| Rv3426 | 232 | | Alpha | Unknown |
| Rv3429 | 178 | | Alpha | Unknown |
| Rv3478 | 393 | | R | Unknown |
| Rv3539 | 479 | | Alpha | Unknown |
| Rv3621c | 413 | | Alpha | Unknown |
| Rv3738c | 315 | | R | Unknown |
| Rv3739c | 77 | | R | Unknown |
| Rv3873 | 368 | | R | Unknown |
| Rv3892c | 399 | | R | Unknown |

[a]Microarray data were obtained from Tuberculist (genolist.pasteur.fr/TuberculList/).
[b]In silico analysis was carried out using the Protein analysis software, PROTEAN, DNASTAR. (R indicates irregular or random structure).

Figure 2:
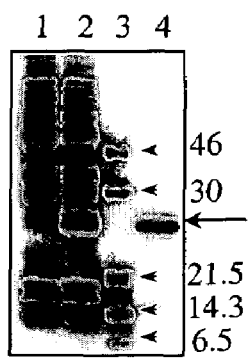

Recombinant Rv2430c protein, folded on-column, does not aggregate upon dialysis: The on-column refolding strategy has been earlier used to facilitate minimal protein aggregation and precipitation. Chemical chaperones such as L-arginine together with Glutathione provide reducing equivalents during folding. This strategy resulted in about 2 mg pure protein per 100 ml culture. Fractions eluted from the purification column were analysed on 12% SDS-PAGE (FIG. 2) which confirmed the homogeneity (>95%) of the recombinant protein. No visible precipitation of the protein was observed upon extensive dialysis and high speed centrifugation (13000 rpm, 15 minutes) pointing to the stable conformation of the refolded protein.

Figure 3:
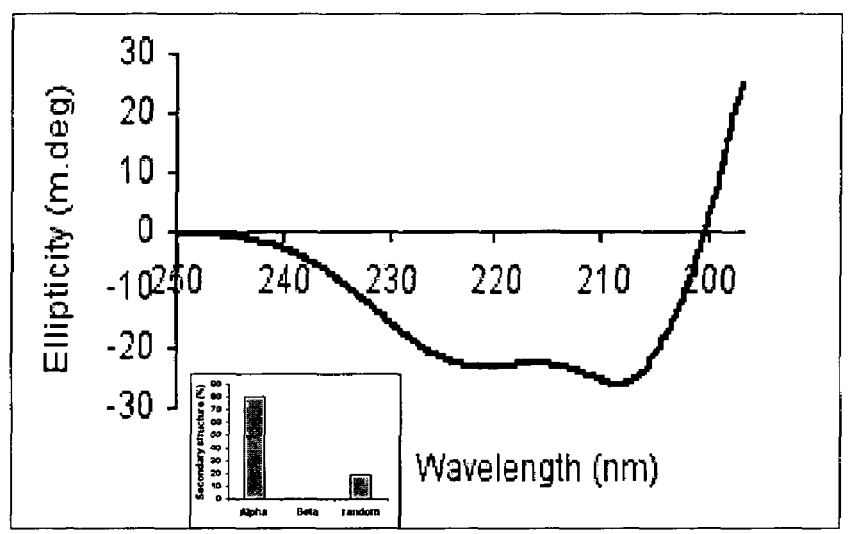
Figure 4:
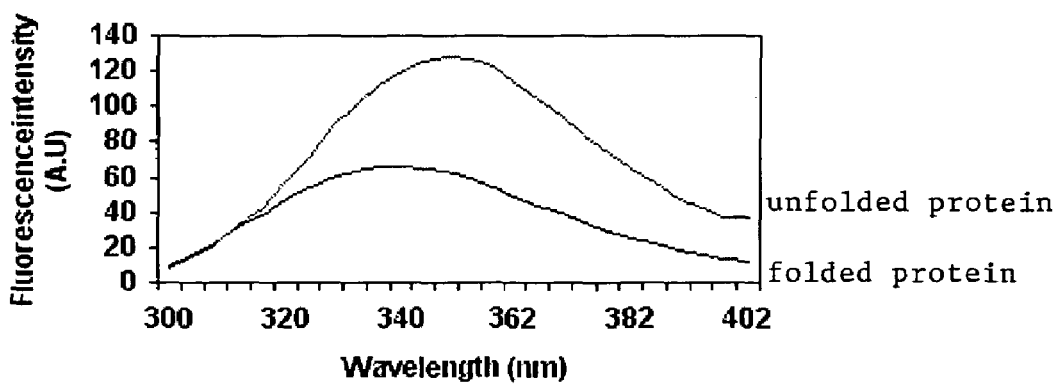

Rv2430c displays α significant α helical composition: The secondary structure of the on-column refolded protein was characterized by Circular Dichroism spectroscopy (CD). The observed CD spectrum was characteristic of a helical protein (FIG. 3). Data obtained from the CD spectra recorded in the 200-250 nm range were used to calculate the secondary structure composition of the protein using the web based programme K2D. The recombinant protein displays 81% α helical content and 19% random coil structure (Inset-FIG. 3). While these data confirm the proper folding of the purified protein, they are in agreement with the in silico predictions that Rv2430c is a predominantly a helical protein. The flourescence spectra of the folded protein differ significantly from the unfolded protein: In order to assess the local environment of the aromatic residues, the folded protein was subjected to urea denaturation followed by fluorescence emission spectra. The refolded PPE protein displayed the emission maximum at 340 nm suggesting that the aromatic amino acid residues are buried in the protein, indicative of a folded protein. A significant red-shift in the absorption maxima and increased emission intensity was observed from 340 nm to 350 nm upon denaturation of protein with 8M urea (FIG. 4). These data suggest that in the native confirmation of the protein, aromatic residues are present in a hydrophobic environment, which become exposed upon protein denaturation.

Figure 6:
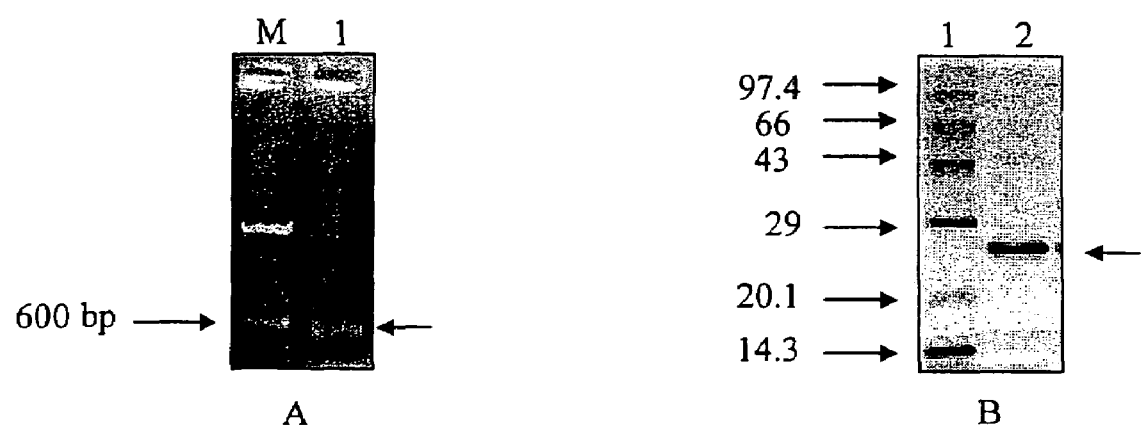

The hypothetical PPE ORF Rv2430c has a high antigenicily profile score and is expressed at the mRNA level. In silico analyses of the PPE ORFs, equal to or less than 200 amino acids in length, belonging to the subgroup 3 of the PPE family (30) was carried out. Rv2430c and Rv3425 displayed major antigenic stretches (FIG. 5) with peak values greater than or equal to 3.0. However, an analysis of the microarray expression data (47) identified Rv2430c as one of the overexpressed genes in an IdeR mutant of *Mycobacterium tuberculosis* and was thereby implicated in pathogenesis. Rv2430c was thus selected for our study. Rv2430c was further subjected to detailed analysis to predict its likely structure through various algorithms. Predict protein server (embl-heidelberg.de/predictprotein) gave a very low score for Rv2430c pointing to the unlikely possibility of this ORF being a transmembrane protein (data not shown). To check whether the hypothetical Rv2430c indeed represented a functional gene, the mRNA extracted from in vitro cultured $H_{37}Rv$ cells was used as a template for reverse transcription followed by PCR. The RT-PCR reaction product was fractionated on a 1% agarose gel. A 597 bp band was observed upon staining with ethidium bromide indicating the expression of this ORF at the mRNA level in the liquid cultures of M.tuberculosis (FIG. 6A). The ORF Rv2430c was expressed as a his-tagged fusion protein in E.coli (FIG. 6B) and used for immunological studies.

The recombinant PPE protein Rv2430c displays strong B-cell responses during infection with tuberculosis. Having shown that the ORF encoded by the PPE family of M. tuberculosis was expressed at the mRNA level, experiments were designed to evaluate the immune response of TB patients to recombinant Rv2430c PPE protein. For this the recombinant Rv2430c protein was used to screen the TB patient sera by enzyme linked immunosorbant assay (ELISA) using anti-human IgG-HRP and anti-human IgM-HRP as conjugates. The humoral immune responses directed against the recombinant protein were compared between patients with tuberculosis and healthy controls. The data (FIG. 7) reveal that sera of all the infected patients mounted a significantly higher antibody responses against Rv2430c as compared to that of the healthy controls ($p<0.0001$). Since negligible antibody responses were obtained in the healthy control group (FIG. 7), it is likely that this protein is expressed during the course of M.tuberculosis infection and may be associated with disease manifestation and progression.

Immunodominant nature of Rv2430c. Since all the patients infected with tuberculosis revealed a strong humoral response against Rv2430c as compared to the healthy control it was of interest to compare the antibody responses between various clinical categories and also to evaluate whether Rv2430c is immunodominant. For this we chose recombinant Hsp10 of M.tuberculosis which is a well known immunodominant antigen of M.tuberculosis (51). FIG. 8 clearly shows that strong antibody responses were elicited against Rv2430c in all the three study groups (Category 1, Category 2 and Category 3). Rv2430c elicited statistically significant immune response as compared to Hsp10 ($p<0.003$) in patients with fresh infection (FIG. 8A). Patients belonging to category 2 and 3 exhibited Rv2430c specific antibody equivalent to Hsp10 (FIGS. 8B and 8C). Since the Purified Protein Derivative (PPD) antigen of M.tuberculosis is also used to diagnose TB infection (2, 15, 29), we compared the immunopotentiality of Rv2430c over PPD only in case of fresh infection (FIG. 8A). Results clearly indicated that the PPE protein Rv2430c is by far more immunogenic and could elicit a stronger B cell responses than the PPD. Sera from fresh infection category responded better against the Rv2430c antigen as compared to PPD, $p<0.0001$ (FIG. 8A).

In order to compare the serological sensitivity of Rv2430c over Hsp10 the data presented in FIG. 8 were recalculated as percentage individuals showing absorbance above 0.65 at 492 nm. Although only 28.12% of individuals with fresh infection mounted strong antibody responses of IgG type to Hsp10, a very high percentage of individuals (62.5%) recognized Rv2430c (FIG. 9A). Similar conclusions could be drawn when IgM antibodies were assayed (Rv2430c vs Hsp10: 71% vs 37.5%, FIG. 9B). From these results, it is apparent that as compared to relapsed or extrapulmonary TB patients, Rv2430c shows better reactivity vis-a-vis Hsp10 to sera from patients with fresh infection. Our results therefore convincingly demonstrate the immunodominant nature of the hypothetical PPE ORF Rv2430c.

The PE and the PPE protein families of M tuberculosis possibly represent principle source of antigenic variation. A few studies have supported the notion that they are involved in eliciting an immune response. However there is no information on the structural features of these proteins. DNA microarray studies have demonstrated that Rv2430c is one of the genes induced in an IdeR mutant [17] and $Rel_{Mtb}$ knock out of M.tuberculosis [18]. In the latter case it has been classified as a probable antigen. However, in-vitro transcription and translation of Rv2430c in a coupled transcription-translation system (Promega, USA) showed that Rv2430c protein is not a membrane bound protein.

We have reported the involvement of Rv2430c in eliciting an immune response in a clinical setting using a panel of sera obtained from three well classified categories of patients. The present study was carried out to gain insights into the structural characteristics of the recombinant PPE protein. Secondary structure prediction employing Protean 4.0 revealed a very high content of α-helical structure in Rv2430c. This is evident from both the Garnier-Robson and Chou-Fasman methods of secondary structure prediction (FIG. 1A). Web based analysis of Rv2430c using PSIPRED (FIG. 1B) and Predict protein also suggested a predominant α helical composition. To confirm these predictions, the recombinant PPE protein was extracted under denaturing conditions from E.coli as expression of the protein led to its localization in the inclusion bodies. Initial attempts to refold the protein using dialysis resulted in massive precipitation of the protein. Therefore, an on-column refolding strategy was used in the presence of L-arginine that is known to act as a chemical chaperone [19, 20], and glutathione was included to provide reducing equivalents during folding. On column refolded protein was soluble and was found to be pure by SDS-PAGE analysis. The purified protein displayed a CD spectra—characteristic of α helical proteins, confirming the in silico predictions of secondary structure. We also tested the possible environment of the aromatic amino acid residues in refolded protein the refolded protein exhibited emission maximum at 340 nm. Interestingly, incubation of protein with urea resulted in the significant red-shift (340 to 350 nm) in the emission maxima and also an increase in the fluorescence intensity was observed, indicating that the aromatic amino acid residues are present in an hydrophobic environment. Thus, there appears to be a well-formed hydrophobic core in the protein, which becomes exposed under the influence of 8 M urea. In the absence of any functional assay described for this protein, conformation of the protein analyzed by CD and Fluorescence studies compared with in silico predictions of protein based on primary structure suggest that the protein is properly folded.

The current method of refolding can be employed for other members of the PE/PPE protein family to obtain large quantities of protein for crystallization purposes. Such on-column refolding strategy has been successfully used for a protein which is known to generate oligomers [21]. That such properly folded protein will likely display differential immunoreactivity to patient sera [16] renders it possible to evaluate other members of this family for their likely biological roles.

The 69 members of the PPE protein family have a conserved N-terminal domain that comprises ~180 amino acids followed by C-terminal segments that vary markedly in sequence and length (30). Based on our pattern search analysis of the Tuberculist database (genolist.pasteur.fr/Tuberculist) these proteins were categorised into three groups, Subgroup 1, represented by 20 members, constitutes the MPTR class characterized by the presence of multiple, tandem copies of the motif Asn-X-Gly-X-Gly-Asn-X-Gly. The second subgroup, comprising of 21 members, contains a characteristic well conserved motif Gly-X-X-Ser-Val-Pro-X-X-Trp around position 350, and the third subgroup proteins, with 28 members, are unrelated except for the presence of the common PPE domain. The Rv2430c belongs to the third subgroup. ORFs belonging to the third subgroup with coding capacity equal to or less than 200 amino acids were shortlisted. This shortlist was further narrowed down based on two very important criteria—namely, antigenic profile and the association of the ORF with pathological conditions as evident from DNA Microarray expression data (47). Rv2430c and Rv3425 were the ORFs with the highest antigenicity index. DNA Microarray results demonstrated that of these two ORFs, Rv2430c was one of the genes induced in IdeR mutant of *Mycobacterium tuberculosis* (47), pointing to its possible role in pathogenesis. Rv2430c was accordingly short listed for the present study and was evaluated for its role as an antigen in a clinical setting.

This ORF was shown to be RT-PCR positive pointing to the likelihood that it may be expressed during infection. The Rv2430c ORF was expressed in *E.coli* and the recombinant protein was purified and tested for its ability to recognize IgG antibody in the sera of tuberculosis patients and healthy individuals.

The TB patients used in our study represent a heterogenous population including fresh infection cases characterized by patients who contracted the pathogen for the first time (Category 1), relapsed cases in which the disease resurfaced after the completion of the treatment (Category 2) and extra-pulmonary cases which are mostly sputum negative (Category 3). The immune response profile of Rv2430c between different clinical categories was studied. The PPE protein Rv2430c was found to be recognized by antibodies in the sera of infected patients in ELISA with a serum dilution of 1:200 whereas a poorer ELISA reactivity was observed in all healthy individuals. The presence of antibodies to Rv2430c in sera from TB patients (FIG. 7) and their absence in sera from healthy individuals suggests that the protein is expressed in vivo during active infection with *M. tuberculosis* and the native molecule is immunogenic.

Several reports have emphasized on the observation of lack of sufficient immune responses in TB patients against many promising serodiagnostic antigens of *M.tuberculosis*. The fact is more distressing in case of fresh infection where for majority of the cases the immune system is not sufficiently primed to elicit a strong antibody responses against most of the *M.tuberculosis* antigens. The recombinant Rv2430c protein was very strongly recognized by all the three categories of patients including also the fresh infection group (Category 1). The members of the heat shock protein family including Hsp70 (43, 51) and Hsp10 (51) have been known to elicit strong B cell response. Surprisingly, in our study the immunodominant antigen Hsp10, though recognized by Category 2 and 3 patients sera, was not sensitive enough to detect the patients having fresh infection (Category 1). The picture remained unaltered when we used PPD in place of Hsp10. It is pertinent to note that although several antigens have been tested for their use in serodiagnosis, no test with single antigen has proved to be able to achieve sensitivity and specificity in a study population suitably large and heterogenous (26, 28, 32, 34, 36, 37, 39, 40, 41, 42, 44, 45). The factors responsible include a) the stage of the disease, b) the location of the infection and c) the genetic background. Our results show that PPE protein Rv2430c, which lacks a transmembrane domain and is therefore likely to be cytosolic or secretory in localization, is an immunodominant B-cell target antigen with apparent diagnostic potential. It would also be interesting to speculate on the use of Rv2430c along with other immunodominant antigens (33) for vaccine development.

REFERENCES

1. S. T. Cole, et al, Deciphering the biology of *Mycobacterium tuberculosis* from the complete genome sequence, Nature. 393 (1998) 537-444.
2. L. Ramakrishnan, N. A. Federspiel, S. Falkow, Granuloma-specific expression of *Mycobacterium virulence proteins from the glycine-rich PE-PGRS family*, Science. 288 (2000)1436-1439.
3. S. Banu, N. Honore, B. Saint-Joanis, D. Philpott, M. C. Prevost, S. T. Cole, Are the PE-PGRS proteins of *Mycobacterium tuberculosis* variable surface antigens?, Mol Microbiol. 44(2002) 9-19.
4. C. Abou-Zeid, T. Garbe, R. Lathigra, H. G. Wiker, M. Harboe, G. A. Rook, D. B. Young, Genetic and immunological analysis of *Mycobacterium tuberculosis* fibronectin-binding proteins, Infect Immun. 59 (1991) 2712-2718.
5. G. Delogu, M. J. Brennan, Comparative immune response to PE and PE_PGRS antigens of *Mycobacterium tuberculosis*, Infect Immun. 69 (2001) 5606-5611.
6. C. Espitia, J. P. Laclette, M. Mondragon-Palomino, A. Amador, J. Campuzano, A. martens, M. Singh, R. Cicero, Y. Zhang, C. Moreno, The PE-PGRS glycine-rich proteins of *Mycobacterium tuberculosis:* a new family of fibronectin-binding proteins?, Microbiology. 145 (1999) 3487-3495.
7. K. K. Singh, X. Zhang, A. S. Patibandla, P. Chien, Jr, S. Laal, Antigens of *Mycobacterium tuberculosis* expressed during preclinical tuberculosis: serological immunodominance of proteins with repetitive amino acid sequences, Infect Immun. 69 (2001) 4185-4191.
8. M. J. Brennan, G. Delogu, Y. Chen, S. bardarov, M. Kriakov, M. Alavi, W. R. Jacobs, Jr, Evidence that mycobacterial PE-PGRS proteins are cell surface constituents that influence interactions with other cells, Infect Immun. 69 (2001) 7326-7333.
9. S. L. Sampson, P. Lukey, R. M. warrem, P. D. van Helden, M. Richardson, M. J. Everett, Expression, characterization and subcellular localization of the *Mycobacterium tuberculosis* PPE gene Rv1917c, Tuberculosis (Edinb). 81(2001) 305-317.
10. D. R. Ronning, T. Klabunde, G. S. Besra, V. D. Vissa, J. T. Belisle, J. C. Sacchettini,_Crystal structure of the secreted form of antigen 85C reveals potential targets for mycobacterial drugs and vaccines, Nat Struct Biol. 7 (2000) 141-146.
11. D. H. Anderson, G. Harth, M. A. Horwitz, D. Eisenberg, An interfacial mechanism and a class of inhibitors inferred from two crystal structures of the *Mycobacterium tuberculosis* 30 kDa major secretory protein (Antigen 85B), a mycolyl transferase, J Mol Biol. 307 (2001) 671-681.
12. P. S. Renshaw, P. Panagiotidou, A. Whelan, S. V. Gordon, R. G. Hewinson, R. A. Williamson, M. D. Carr, Conclusive evidence that the major T-cell antigens of the *Mycobacterium tuberculosis* complex ESAT-6 and CFP-10 form a tight 1:1 complex and characterisation of the structural properties of ESAT-6, CFP-10 and the ESAT- 6.CFP-10 complex. Implications for pathogenesis and virulence, J. Biol. Chem. 277 (2002) 21598-21603.
13. M. J. Bloemink, J. Kemmink, E. Dentton, F. W. Muskett, A. Whelan, A. Sheihk, G. Hewinson, R. A. Williamson, M. D. Carr, Sequence-specific assignment and determination of the secondary structure of the 163 residue M.tuberculosis and M.bovis antigenic protein mpb70, J. Biomol. NMR. 20 (2001) 185-186.
14. C. W. Goulding, A. Parseghian, M. R. Sawaya, D. Cascio, M. I. Apostol, M. L. Gennaro, D. Eisenberg, Crystal structure of a major secreted protein of Mycobacterium tuberculosis-MPT63 at 1.5-A resolution, Protein Sci. 11 (2002) 2887-2893.
15. K. R. Devikumar, K. S. Kumar, B. Ramalingam, R. Alamelu, Purification and characterization of three immunodominant proteins (38, 30, and 16 kDa) of Mycobacterium tuberculosis, Protein Expr Purif. 24 (2002) 188-195.
16. R. K. Choudhary, S. Mukhopadhyay, P. Chakhaiyar, N. Sharma, K. J. Murthy, V. M. Katoch, S. E. Hasnain, PPE antigen Rv2430c of Mycobacterium tuberculosis induces a strong B-cell response, Infect Immun. 71(2003) 6338-6343.
17. G. M. Rodriguez, M. I. Voskuil, B. Gold, G. K. Schoolnik, I, Smith, ideR, An essential gene in Mycobacterium tuberculosis: role of IdeR in iron-dependent gene expression, iron metabolism, and oxidative stress response, Infect Immun. 70 (2002) 3371-3381.
18. J. L. Dahl, C. N. Kraus, H. I. Boshoff, B. Doan, K. Foley, D. Avarbock, G. Kaplan, V. Mizrahi, H. Rubin, C. E. Barry $3^{rd}$, The role of RelMtb-mediated adaptation to stationary phase in long-term persistence of Mycobacterium tuberculosis in mice, Proc. Natl. Acad. Sci. U S A. 100 (2003) 10026-10031.
19. E. E. Boeggeman, B. Ramakrishnan, P. K. Qasba, The N-terminal stem region of bovine and human beta 1,4-galactosyltransferase I increases the in vitro folding efficiency of their catalytic domain from inclusion bodies, Protein Expr Purif. 30 (2003) 219-229.
20. V. Srinivas, B. Raman, K. S. Rao, T. Ramakrishna, Ch. M. Rao, Structural perturbation and enhancement of the chaperone-like activity of alpha-crystallin by arginine hydrochloride, Protein Sci. 12 (2003) 1262-70.
21. R. Pullakhandham, S. Ghosh, K. Soundarya, A. Haseeb, B. Aruna, N. Z. Ehtesham, Dimerization of human recombinant resistin involves covalent and non-covalent interactions, Biochem Biophys Res Commun, 313(2004) 652-656
22. J. C. Betts, P. T. Lukey, L. C. Robb, R. A. McAdam, K. Duncan, Evaluation of a nutrient starvation model of Mycobacterium tuberculosis persistence by gene and protein expression profiling, Mol. Microbiol, 43(2002) 713-731.
23. M. A. Fisher, B. B. Plikaytis, T. M. Shinnick, Microarray analysis of the Mycobacterium tuberculosis transcriptional response to the acidic conditions found in phagosomes, J Bacteriol, 184(2002) 4025-4032.
24. Abou-Zeid, C., T. Garbe, R. Lathigra, H. G. Wiker, M. Harboe, G. A. Rook, and D. B. Young. 1991. Genetic and immunological analysis of Mycobacterium tuberculosis fibronectin-binding proteins. Infect. Immun. 59:2712-2718.
25. Almeida, L., M., M. A. Barbieri, A. C. Da Paixao, L. E. Cuevas. 2001. Use of purified protein derivative to assess the risk of infection in children in close contact with adults with tuberculosis in a population with high Calmette-Guerin bacillus coverage. Pediatr Infect Dis J. 20:1061-5.
26. Amara, R. R., S. Shanti, and V. Satchidanandam. 1998. Characterization of novel immunodominant antigens of Mycobacterium tuberculosis. Microbiology. 144:1197-1203.
27. Banu, S., N. Honore, B. Saint-Joanis, D. Philpott, M. C. Prevost, and S. T. Cole. 2002. Are the PE-PGRS proteins of Mycobacterium tuberculosis variable surface antigens? Mol. Microbiol. 44:9-19.
28. Batoni, G., D. Bottai, S. Esin, W. Florio, M. Pardini, G. Maisetta, G. Freer, S. Senesi, and M. Campa. 2002. Purification, biochemical characterization and immunogenicity of SA5K, a secretion antigen of Mycobacterium tuberculosis. Scand J Immunol. 56:43-51.
29. Brennan, M. J., G. Delogu, Y. Chen, S. Bardarov, J. Kriakov, M. Alavi, and W. R. Jacobs Jr. 2001. Evidence that mycobacterial PE_PGRS proteins are cell surface constituents that influence interactions with other cells. Infect. Immun. 69:7326-7333.
30. Cole, S. T. et al. 1998. Deciphering the biology of Mycobacterium tuberculosis from the complete genome sequence. Nature 393:537-544.
31. Delogu, G., and M. J. Brennan. 2001. Comparative immune response to PE and PE_PGRS antigens of Mycobacterium tuberculosis. Infect. Immun. 69:5606-5611.
32. Devi, K. R., K. S. Kumar, B. Ramalingam, and R. Alamelu. 2002. Purification and characterization of three immunodominant proteins (38, 30, and 16 kDa) of Mycobacterium tuberculosis. Protein Expr Purif. 24:188-195.
33. Dhar, N., V. Rao, and A. K. Tyagi. 2000. Recombinant BCG approach for development of vaccines: cloning and expression of immunodominant antigens of Mycobacterium tuberculosis. FEMS Microbiol Lett. 190:309-316.
34. Dillon, D. C., M. R. Alderson, C. H. Day, T. Bement, A. Campos-Neto, Y. A. Skeiky, T. Vedvick, R. Badaro, S. G. Reed, and R. L. Houghton. 2000. Molecular and immunological characterization of Mycobacterium tuberculosis CFP-10, an immunodiagnostic antigen missing in Mycobacterium bovis BCG. J. Clin. Microbiol. 38:3285-3290.
35. Espitia, C., J. P. Laclette, M. Mondragon-Palomino, A. Amador, J. Campuzano, A. Martens, M. Singh, R. Cicero, Y. Zhang, and C. Moreno. 1999. The PE-PGRS glycine-rich proteins of Mycobacterium tuberculosis: a new family of fibronectin-binding proteins? Microbiology. 145: 3487-3495.
36. Florio, W., D. Bottai, G. Batoni, S. Esin, M. Pardini, G. Maisetta, and M. Campa. 2002. Identification, molecular cloning, and evaluation of potential use of isocitrate dehydrogenase II of Mycobacterium bovis BCG in serodiagnosis of tuberculosis. Clin. Diagn. Lab. Immunol. 9:846-851.
37. Houghton, R. L., M. J. Lodes, D. C. Dillon, L. D. Reynolds, C. H. Day, P. D. McNeill, R. C. Hendrickson, Y. A. Skeiky, D. P. Sampaio, R. Badaro, K. P. Lyashchenko, and S. G. Reed. 2002. Use of multiepitope polyproteins in serodiagnosis of active tuberculosis. Clin. Diagn. Lab. Immunol. 9:883-891.
38. Kalish, S.B., R. C. Radin, J. P. Phair, D. Levitz, C. R. Zeiss, E. Metzger. 1983. Use of an enzyme-linked immunosorbent assay technique in the differential diagnosis of active pulmonary tuberculosis in humans. J Infect Dis. 147(3):523-30.
39. Laal, S., K. M. Samanich, M. G. Sonnenberg, S. Zolla-Pazner, J. M. Phadtare, and J. T. Belisle. 1997. Human humoral responses to antigens of Mycobacterium tuber- 40. Lim, R. L., L. K. Tan, W. F. Lau, M. C. Ming, R. Dunn, H. P. Too, and L. Chan. 2000. Cloning and expression of immunoreactive antigens from *Mycobacterium tuberculosis*. Clin. Diagn. Lab. Immunol. 7:600-606.
41. Ljungqvist, L., A. B. Andersen, P. Andersen, K. Haslov, A. Worsaae, J. Bennedsen, and I. Heron. 1990. Affinity purification, biological characterization and serological evaluation of defined antigens from *Mycobacterium tuberculosis*. Trop. Med. Parasitol. 41:333-335.
42. Lodes, M. J., D. C. Dillon, R. Mohamath, C. H. Day, D. R. Benson, L. D. Reynolds, P. McNeill, D. P. Sampaio, Y. A. Skeiky, R. Badaro, D. H. Persing, S. G. Reed, and R. L. Houghton. 2001. Serological expression cloning and immunological evaluation of MTB48, a novel *Mycobacterium tuberculosis* antigen. J. Clin. Microbiol. 39:2485-2493.
43. Mehlert, A., and D. B. Young. 1989. Biochemical and antigenic characterization of the *Mycobacterium tuberculosis* 71 kD antigen, a member of the 70 kD heat-shock protein family. Mol. Microbiol. 3:125-130.
44. Mustafa, A. S., P. J. Cockle, F. Shaban, R. G. Hewinson, and H. M. Vordermeier. 2002. Immunogenicity of *Mycobacterium tuberculosis* RD1 region gene products in infected cattle. Clin. Exp. Immunol. 130:37-42.
45. Mustafa, A.,S. Development of new vaccines and diagnostic reagents against tuberculosis. 2002. Mol. Immunol. 39:113-9.
46. Ramakrishnan, L., N. A. Federspiel, S. Falkow. 2000. Granuloma-specific expression of *Mycobacterium* virulence proteins from the glycine-rich PE-PGRS family. Science. 288:1436-1439.
47. Rodriguez, G. M., M. I. Voskuil, B. Gold, G. K. Schoolnik, I. Smith. 2002. IdeR, An essential gene in *mycobacterium tuberculosis*: role of IdeR in iron-dependent gene expression, iron metabolism, and oxidative stress response. Infect. Immun. 70(7):3371-81.
48. Sampson, S. L., P. Lukey, R. M. Warren, P. D. van Helden, M. Richardson and M. J. Everett. 2001. Expression, characterization and subcellular localization of the *Mycobacterium tuberculosis* PPE gene Rv1917c. Tuberculosis (Edinb). 81:305-17.
49. Siddiqi, N., M. Shamim, S. Hussain, R. K. Choudhary, N. Ahmed, Prachee, S. Banerjee, G. R. Savithri, M. Alam, N. Pathak, A. Amin, M. Hanief, V. M. Katoch, S. K. Sharma, and S. E. Hasnain. 2002. Molecular characterization of multidrug-resistant isolates of *Mycobacterium tuberculosis* from patients in North India. Antimicrob. Agents. Chemother. 46:443-450.
50. Singh, K. K., X. Zhang, A. S. Patibandla, P. Chien Jr, and S. Laal. 2001. Antigens of *Mycobacterium tuberculosis* expressed during preclinical tuberculosis: serological immunodominance of proteins with repetitive amino acid sequences. Infect Immun. 69:4185-4191.
51. Young, D. B., and T. R. Garbe. 1991. Heat shock proteins and antigens of *Mycobacterium tuberculosis*. Infect Immun. 59:3086-93.
52. Zeiss, C.,R., S. B. Kalish, K. S. Erlich, D. Levitz, E. Metzger, R. Radin, J. P. Phair. 1984. IgG antibody to purified protein derivative by enzyme-linked immunosorbent assay in the diagnosis of pulmonary tuberculosis. Am Rev Respir Dis. 130:845-8.

---

The invention claimed is:

1. A PPE family antigenic protein Rv2430c, the amino acid sequence of which consists of the sequence set forth in SEQ ID No. 1.

2. A protein as claimed in claim 1, wherein the protein shows a strong B-cell immune response.

3. A protein as claimed in claim 1, wherein the protein has a high content of alpha helices.

4. A protein as claimed in claim 1, wherein the protein is more antigenic than Hsp 10 and PPD.

5. A set of three high antigenic index peptides, the amino acid sequences of which consist of the sequence set forth in SEQ ID Nos. 2 to 4.

6. An antigenic ORF Rv2430c, consisting of the amino acid sequence which is encoded by SEQ ID NO:5.

7. A method of inducing an immune response against *Mycobacterium tuberculosis* in a subject in need thereof, said method comprising the steps of:
   a. introducing PPE antigenic protein Rv2430c, the amino acid sequence of which consists of the sequence set forth in SEQ ID No. 1 into the subject and
   b. inducing an immune response against *Mycobacterium tuberculosis*.

8. A method as claimed in claim 7, wherein the subject shows a strong B-cell immune response.

9. A method as claimed in claim 7, wherein the subject is an animal or human being.

* * * * *

SEQUENCE LISTING

<160> NUMBER OF SEQ ID NOS: 10

<210> SEQ ID NO 1
<211> LENGTH: 194
<212> TYPE: PRT
<213> ORGANISM: M. tuberculosis

<400> SEQUENCE: 1

```
Met His Phe Glu Ala Tyr Pro Pro Glu Val Asn Ser Ala Asn Ile Tyr
1               5                   10                  15

Ala Gly Pro Gly Pro Asp Ser Met Leu Ala Ala Arg Ala Trp Arg
            20                  25                  30

Ser Leu Asp Val Glu Met Thr Ala Val Gln Arg Ser Phe Asn Arg Thr
        35                  40                  45

Leu Leu Ser Leu Met Asp Ala Trp Ala Gly Pro Val Val Met Gln Leu
    50                  55                  60

Met Glu Ala Ala Lys Pro Phe Val Arg Trp Leu Thr Asp Leu Cys Val
65                  70                  75                  80

Gln Leu Ser Glu Val Glu Arg Gln Ile His Glu Ile Val Arg Ala Tyr
                85                  90                  95

Glu Trp Ala His His Asp Met Val Pro Leu Ala Gln Ile Tyr Asn Asn
            100                 105                 110

Arg Ala Glu Arg Gln Ile Leu Ile Asp Asn Asn Ala Leu Gly Gln Phe
        115                 120                 125

Thr Ala Gln Ile Ala Asp Leu Asp Gln Glu Tyr Asp Asp Phe Trp Asp
```

|  |  |  |  | 130 |  |  |  | 135 |  |  |  | 140 |  |  |
|---|---|---|---|---|---|---|---|---|---|---|---|---|---|---|
| Glu | Asp | Gly | Glu | Val | Met | Arg | Asp | Tyr | Arg | Leu | Arg | Val | Ser | Asp | Ala |
| 145 |  |  |  | 150 |  |  |  |  |  | 155 |  |  |  | 160 |  |

| Leu | Ser | Lys | Leu | Thr | Pro | Trp | Lys | Ala | Pro | Pro | Ile | Ala | His | Ser |
|---|---|---|---|---|---|---|---|---|---|---|---|---|---|---|
|  |  |  |  | 165 |  |  |  |  | 170 |  |  |  | 175 |  |

| Thr | Val | Leu | Val | Ala | Pro | Val | Ser | Pro | Ser | Thr | Ala | Ser | Ser | Arg | Thr |
|---|---|---|---|---|---|---|---|---|---|---|---|---|---|---|---|
|  |  |  | 180 |  |  |  |  | 185 |  |  |  |  | 190 |  |  |

Asp Thr

<210> SEQ ID NO 2
<211> LENGTH: 11
<212> TYPE: PRT
<213> ORGANISM: M. tuberculosis

<400> SEQUENCE: 2

Ala Val Gln Arg Ser Phe Asn Arg Thr Leu Leu
1               5                   10

<210> SEQ ID NO 3
<211> LENGTH: 11
<212> TYPE: PRT
<213> ORGANISM: M. tuberculosis

<400> SEQUENCE: 3

Tyr Asn Asn Arg Ala Glu Arg Gln Ile Leu Ile
1               5                   10

<210> SEQ ID NO 4
<211> LENGTH: 10
<212> TYPE: PRT
<213> ORGANISM: m. tuberculosis

<400> SEQUENCE: 4

Pro Ser Thr Ala Ser Ser Arg Thr Asp Thr
1               5                   10

<210> SEQ ID NO 5
<211> LENGTH: 585
<212> TYPE: DNA
<213> ORGANISM: m. tuberculosis

<400> SEQUENCE: 5

| atgcatttcg | aagcgtaccc | accggaggtc | aactccgcca | acatatatgc | cggccccggt | 60 |
|---|---|---|---|---|---|---|
| cctgactcga | tgttggctgc | cgccagggcg | tggaggtcgt | tggatgtgga | aatgacggcc | 120 |
| gtgcagaggt | cgttcaaccg | aacgctgctg | tctctgatgg | acgcctgggc | gggtccagtg | 180 |
| gtgatgcagt | tgatggaggc | agccaagccg | tttgtcaggt | ggctgaccga | cctctgtgtg | 240 |
| cagctgtctg | aggtcgagag | gcagatccac | gagatcgtgc | gggcctatga | atgggcacat | 300 |
| cacgatatgg | tgcccctggc | gcagatctac | aacaaccgtg | ctgagaggca | gattctgatc | 360 |
| gacaacaacg | cgcttgggca | attcactgcg | cagatcgccg | acctcgacca | agaatatgac | 420 |
| gacttctggg | acgaggacgg | agaggtgatg | aggactaca | gcttcgggt | gtcggatgcg | 480 |
| ttgtcgaagt | tgactccgtg | gaaggcgccg | ccgccgatcg | cccacagtac | cgtgttggtc | 540 |
| gcaccggtgt | cacccagcac | ggcgtcatcg | cgtacagaca | cttag |  | 585 |

<210> SEQ ID NO 6
<211> LENGTH: 8
<212> TYPE: PRT
<213> ORGANISM: m. tuberculosis -continued

```
<220> FEATURE:
<221> NAME/KEY: MISC_FEATURE
<222> LOCATION: (1)..(8)
<223> OTHER INFORMATION: X = any amino acid

<400> SEQUENCE: 6

Asn Xaa Gly Xaa Gly Asn Xaa Gly
1               5

<210> SEQ ID NO 7
<211> LENGTH: 9
<212> TYPE: PRT
<213> ORGANISM: m. tuberculosis
<220> FEATURE:
<221> NAME/KEY: MISC_FEATURE
<222> LOCATION: (1)..(9)
<223> OTHER INFORMATION: X = any amino acid

<400> SEQUENCE: 7

Gly Xaa Xaa Ser Val Pro Xaa Xaa Trp
1               5

<210> SEQ ID NO 8
<211> LENGTH: 24
<212> TYPE: DNA
<213> ORGANISM: Artificial sequence
<220> FEATURE:
<223> OTHER INFORMATION: PCR primer

<400> SEQUENCE: 8
ggatccatgc atttcgaagc gtac                                              24

<210> SEQ ID NO 9
<211> LENGTH: 27
<212> TYPE: DNA
<213> ORGANISM: Artificial sequence
<220> FEATURE:
<223> OTHER INFORMATION: PCR primer

<400> SEQUENCE: 9
aagcttctaa gtgtctgtac gcgatga                                           27

<210> SEQ ID NO 10
<211> LENGTH: 194
<212> TYPE: PRT
<213> ORGANISM: m. tuberculosis

<400> SEQUENCE: 10

Met His Phe Glu Ala Tyr Pro Pro Glu Val Asn Ser Ala Asn Ile Tyr
1               5                   10                  15

Ala Gly Pro Gly Pro Asp Ser Met Leu Ala Ala Arg Ala Trp Arg
            20                  25                  30

Ser Leu Asp Val Glu Met Thr Ala Val Gln Arg Ser Phe Asn Arg Thr
        35                  40                  45

Leu Leu Ser Leu Met Asp Ala Trp Ala Gly Pro Val Val Met Gln Leu
    50                  55                  60

Met Glu Ala Ala Lys Pro Phe Val Arg Trp Leu Thr Asp Leu Cys Val
65                  70                  75                  80

Gln Leu Ser Glu Val Glu Arg Gln Ile His Glu Ile Val Arg Ala Tyr
                85                  90                  95

Glu Trp Ala His His Asp Met Val Pro Leu Ala Gln Ile Tyr Asn Asn
            100                 105                 110

Arg Ala Glu Arg Gln Ile Leu Ile Asp Asn Asn Ala Leu Gly Gln Phe
```

-continued

```
            115                 120                 125
Thr Ala Gln Ile Ala Asp Leu Asp Gln Glu Tyr Asp Asp Phe Trp Asp
        130                 135                 140

Glu Asp Gly Glu Val Met Arg Asp Tyr Arg Leu Arg Val Ser Asp Ala
145                 150                 155                 160

Leu Ser Lys Leu Thr Pro Trp Lys Ala Pro Pro Ile Ala His Ser
                165                 170                 175

Thr Val Leu Val Ala Pro Val Ser Pro Ser Thr Ala Ser Ser Arg Thr
            180                 185                 190

Asp Thr
```